United States Patent [19]

Swim et al.

[11] Patent Number: Plant 5,704

[45] Date of Patent: Apr. 1, 1986

[54] HYBRID TEA ROSE PLANT CV. AROFRAP

[75] Inventors: Herbert C. Swim; Jack E. Christensen, both of Ontario, Calif.

[73] Assignee: Armstrong Nurseries, Inc., Ontario, Calif.

[21] Appl. No.: 639,750

[22] Filed: Aug. 13, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A new hybrid tea rose for garden decoration, having as its seed parent Angel Face (U.S. Plant Pat. No. 2,792) and as its pollen parent First Prize (U.S. Plant Pat. No. 2,774). The new cultivar produces an unusual flower color combination of tan centers surrounded by bright pink outer petals. It grows vigorously, displaying an abundance of deep green, semi-glossy foliage. Removal of old blooms to maintain a continual production of flowers during the growing season is not required as the plant is unable to set hips.

1 Drawing Figure

This invention relates to a new variety of hybrid tea rose cv. Arofrap. The plant is a half-hardy, outdoor seedling of medium height, cultivated for garden decoration. It was first propagated by Herbert C. Swim and Jack E. Christensen in Ontario, Calif., having as its seed parent Angel Face (U.S. Plant Pat. No. 2,792) and as its pollen parent First Prize (U.S. Plant Pat. No. 2,774).

Arofrap may be distinguished from other presently commercialized rose cultivars by the following combination of characteristics: its unusual flower color combination of tan centers surrounded by bright pink outer petals; its abundant production of classically formed flowers; its vigorous growth, unusual among rose cultivars with tan flower coloration; its abundance of deep green, semi-glossy foliage that attractively clothes the plant; and its inability to set hips, which permits the plant to maintain a continual production of flowers during the growing season without requiring the removal of old blooms. The new variety holds its distinguishing characteristics through succeeding propagations by budding.

This new rose may be distinguished from its seed parent, Angel Face (U.S. Plant Pat. No. 2,792), by the following combination of characteristics: Angel Face produces flowers of a blended medium-lavender coloration, whereas the new rose produces flowers of a pink and tan coloration, essentially as described and illustrated herein. The seed parent is classified as a hybrid floribunda, whereas the new cultivar is classified as a hybrid tea. Angel Face produces flowers with about 30 wavy petals, whereas the new rose produces flowers with significantly more (35 to 40) broad petals. Arofrap produces flowers of 4 to 4½ inches in diameter, whereas the seed parent produces significantly smaller flowers of 3½ to 4 inches in diameter.

The new cultivar Arofrap may be distinguished from its pollen parent, First Prize (U.S. Plant Pat. No. 2,774), by the following combination of characteristics: First Prize produces flowers of a blended pink coloration, whereas the new cultivar produces flowers of a pink and tan coloration, essentially as described and illustrated herein. The pollen parent produces flowers with about 30 petals, whereas Arofrap produces flowers of significantly higher petalage (35 to 40 petals). Whereas the new rose produces flowers of a 4- to 4½-inch diameter, First Prize produces significantly larger blooms of 5 to 6 inches in diameter.

The accompanying drawing illustrates the new variety in color as grown in Ontario, Calif., and shows the flowering thereof from bud to full bloom.

Throughout this specification, color names beginning with a small letter signify that the name of that color as used in common speech is aptly descriptive. Color names beginning with a capital letter designate values based on The R.H.S. Colour Chart published by The Royal Horticultural Society of London, England.

The descriptive matter which follows pertains to roses grown in Ontario, Calif., and is believed to apply to similar conditions of soil and climate elsewhere.

FLOWER

The new variety bears its flowers sometimes singly, sometimes 3 to 5 flowers per stem, in regular, rounded clusters on normal to strong stems of medium length for the class. Outdoors, the plant blooms nearly continuously and in abundant quantities throughout the growing season. It has a moderate tea to fruity fragrance.

BUD

The peduncle is of average length for the class and of average caliper, strong and erect. It is entirely smooth and has a color between Yellow-Green 144A and Green 136A.

Before the calyx breaks, the bud is of medium size for the class and of medium length, pointed and ovoid in form, with few hairs and stipitate glands on its surface. There are usually slender foliaceous parts extending beyond the tip of the bud equal to one half or more of its length.

As the calyx breaks, the color of the bud is between Red-Purple 60A and Red-Purple 59C. The inner surface of the sepals has a fine, woolly tomentum; the sepal margins are lined with hairs.

As the first petal opens, the bud is average in size for the class, of medium length and pointed to ovoid in form. On the outside of the petals is a small basal attachment zone near Yellow 7B which quickly suffuses to between Red 53D and Red-Purple 59C. On the inside of the petals is a large basal attachment zone near Yellow 7B which slowly suffuses to between Red 55B and Red-Purple 64C. The bud opens up well and is not prevented from opening by cold, hot, wet or dry weather.

BLOOM

The size of the bloom when fully open is average for the class, ranging from 4 to 4½ inches in diameter. The petalage is double with from 35 to 40 petals and from 4 to 8 petaloids, with petals arranged regularly. Bloom form when half open is moderately high-centered to cupped; the petals are moderately spiraled, with petal edges somewhat reflexed outward. When fully open, the bloom is moderately cupped, with petals more loosely cupped; petal edges are moderately reflexed outward.

The petals are of moderately heavy substance, of medium thickness, with slightly shiny to satiny insides and shiny outsides. The outside petals are nearly round to broadly ovate, with rounded apices. The intermediate petals are broadly obovate with rounded apices. The inside petals are nearly obovate with irregular edges. Petal colors may be modified by being bordered or blotched or shaded or washed or tinted with other colors.

The paragraph immediately following describes the color values observed in a flower newly opened in the month of October. The plant described had been grown outdoors in Ontario, Calif.

The outside surface of the outside, intermediate, and inner petals has a small basal attachment zone near Yellow 7B, and the remainder of the petal surface quickly suffuses to between Red 54B and Red-Purple 61D. The inside surface of the outside petals has a large basal attachment zone near Yellow 7B, and the remainder of the petal surface slowly suffuses to between Red 55B and Red 51C. The inside surface of the intermediate petals has a large basal attachment zone near Yellow 7B, and the remainder of the petal surface slowly suffuses to between Greyed-Red 179D and Red 38D; petal edges may be blushed with between Red 55B and Red 51C. The inside surface of the inner petals has the same color as the inside surface of the intermediate petals but without blushing near the petal edges.

The paragraph immediately following describes color values observed in a bloom which had been open for three days in the month of October. The plant described had been grown outdoors in Ontario, Calif.

The outside surface of the outside and inside petals has a small basal attachment zone near Yellow 7D, and the remainder of the petal surface quickly suffuses to between Red 55C and Red-Purple 62A. The inside surface of the outside and inside petals has a large basal attachment zone near Yellow 7C, with the remainder of the petal surface slowly suffusing to between Red 49C and Red 56A; some petal edges blush to between Red-Purple 57D and Red 55B.

The general color effect of the newly opened flower is between Red 55B and Red 51C at the outermost petals, and between Greyed-Red 179D and Red 38D at the innermost petals. After being open three days, the bloom gives a general color effect which is predominantly between Red 49C and Red 56A, with some petal edges washed with between Red-Purple 57D and Red 55B. The petals usually drop off cleanly and are not particularly affected in this respect by hot, wet, or dry weather.

In October, roses grown in the garden last on the bush from 4 to 5 days. Flowers cut from plants grown outdoors in the month of October will last from 4 to 5 days at living-room temperatures.

REPRODUCTIVE ORGANS

There are few to an average number of stamens arranged regularly about the pistils. Filaments are medium to long in length, and most have anthers. The anthers are of medium size, and all open approximately at once. Their color when immature is near Yellow-Orange 15B and near Greyed-Orange 166A when mature. Pollen is somewhat sparse in quantity and near Yellow-Orange 15D in color.

Pistils are average to many in number (approximately 60). The styles are uneven, average in length to long, of average caliper, and somewhat loosely bunched. The stigma is near Yellow 4B in color.

This variety does not normally set hips under Ontario, Calif. growing conditions.

FOLIAGE

The compound leaves are borne in abundant quantities and usually comprise from three to five leaflets. The leaves are of medium size for the class, moderately heavy and semi-glossy in appearance. The leaflets are ovate in shape and have acute apices and round bases. Their margins are simply serrate.

The upper surface of the mature foliage is between Yellow-Green 147A and Green 133A in color; its under surface is between Yellow-Green 147B and Green 138B. The upper surface of the young foliage is between Greyed-Purple 187A and Greyed-Purple 187B in color, and the under surface is between Greyed-Purple 187C and Greyed-Purple 187D.

The rachis is of average size, grooved on its upper side, and with few stipitate glands on the edges. The underside of the rachis is sparsely prickly with some stipitate glands.

The stipules are of medium length, medium in width to wide with moderately long points, usually turning out at an angle of more than 45°.

The plant displays an average resistance to mildew, rust and blackspot as compared to other commercial varieties of roses grown under comparable conditions in Ontario, Calif.

GROWTH

The plant is of medium height, bushy and upright to spreading in habit, and much branched. It displays very vigorous growth. The canes are of medium caliper for the class.

The main stems are between Yellow-Green 146C and Green 133B in color. They bear a few large prickles which are of medium length for the class; there are almost straight to hooked, angled slightly downward, and have broad bases of medium length. Large prickle color is between Greyed-Orange 166C and Greyed-Orange 165C. There are very few small prickles and no hairs on the main stems. Small prickles are of the same color as the large prickles.

The branches are of a color between Yellow-Green 146B and Green 133A. They bear very few large prickles, which are of medium length for the class; like the large stem prickles, these are almost straight to hooked, angled slightly downward, and have broad bases of medium length. Their color is near Greyed-Yellow 162B. The branches have no hairs and very few small prickles of a color near Greyed-Yellow 162B.

New shoots are between Yellow-Green 146B and Green 133B in color, washed heavily with near Greyed-Purple 187A. They bear very few large prickles, which are of medium length for the class. The large prickles are almost straight to hooked and angled slightly downward, with broad bases of medium length; large prickle color is near Greyed-Purple 187B. The new shoots have no hairs and a few small prickles near Greyed-Purple 187B in color.

We claim:

1. A new and distinct variety of rose plant of the hybrid tea class, substantially as herein shown and described, being particularly characterized by its unusual flower color combination of tan centers surrounded by bright pink outer petals; its abundant production of classically formed flowers, its vigorous growth, unusual among rose cultivars with tan flower coloration; its abundance of deep green, semi-glossy foliage that attractively clothes the entire plant; and its inability to set hips, which permits the plant to maintain a continual production of flowers during the growing season without requiring the removal of old blooms.

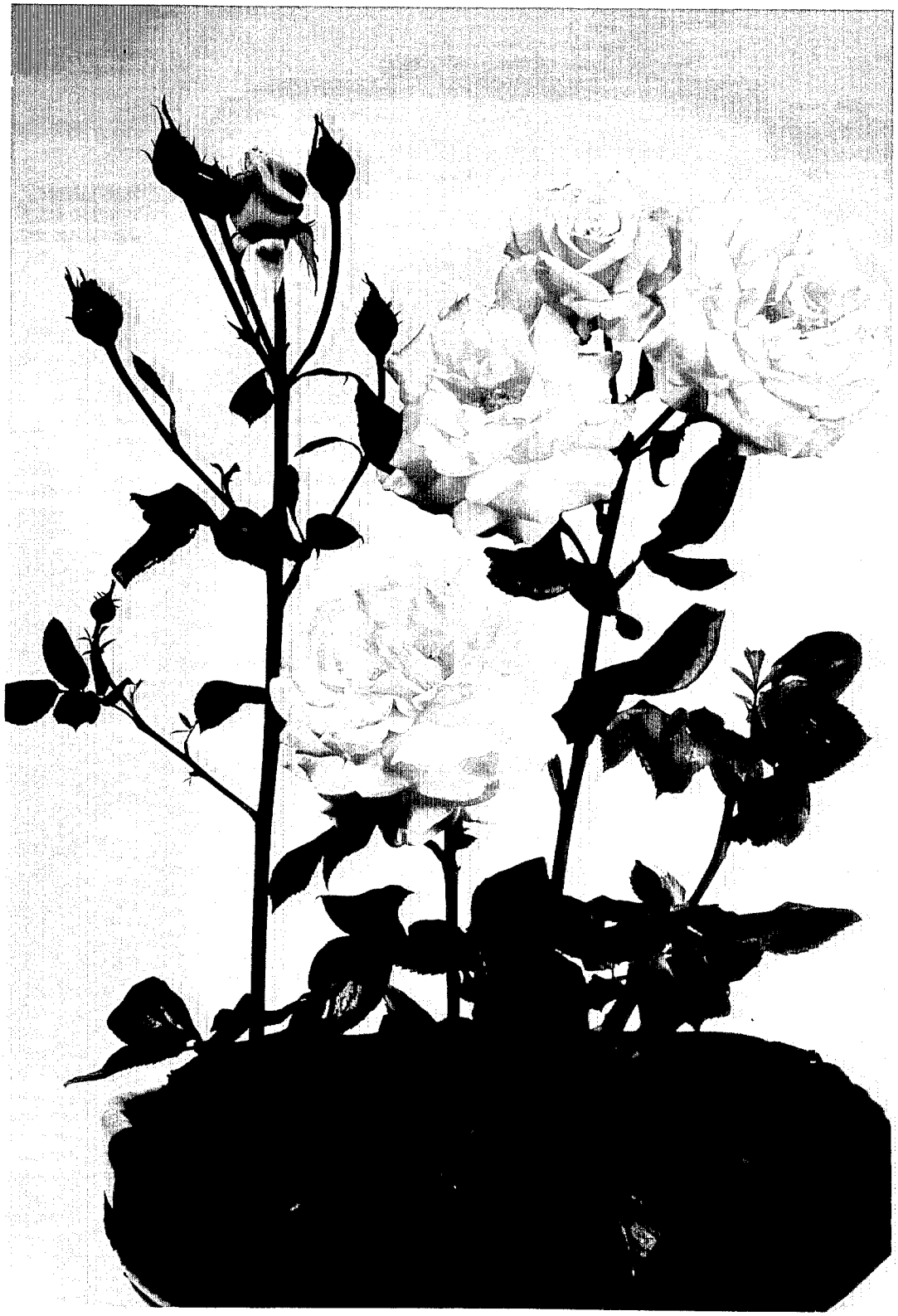

* * * * *